United States Patent [19]
Weiss et al.

[11] Patent Number: 5,892,116
[45] Date of Patent: Apr. 6, 1999

[54] GELATORS

[75] Inventors: Richard G. Weiss, Bethesda, Md.; Liangde Lu, Arlington, Va.

[73] Assignee: Georgetown University, Washington, D.C.

[21] Appl. No.: 778,371

[22] Filed: Jan. 2, 1997

Related U.S. Application Data

[60] Provisional application No. 60/009,647, Jan. 3, 1996.

[51] Int. Cl.[6] .................................................. C07C 211/00
[52] U.S. Cl. .......................... 564/281; 564/282; 564/291; 552/521
[58] Field of Search .............................. 552/521; 564/281

[56] References Cited

U.S. PATENT DOCUMENTS

| | | |
|---|---|---|
| 2,388,887 | 11/1945 | Weissberger et al. . |
| 2,751,284 | 6/1956 | Hill et al. . |
| 2,933,530 | 4/1960 | Kralt et al. ............................ 564/281 |
| 3,084,033 | 4/1963 | Kelly et al. . |
| 3,124,512 | 3/1964 | Schmid et al. ......................... 564/281 |
| 3,413,285 | 11/1968 | Tsafsas ................................. 552/521 |
| 3,424,793 | 1/1969 | Kakosinski et al. ..................... 564/281 |
| 3,507,635 | 4/1970 | Sarem et al. . |
| 3,545,946 | 12/1970 | Hiatt et al. . |
| 3,557,214 | 1/1971 | Koenig et al. ......................... 564/281 |
| 3,562,266 | 2/1971 | Minisci et al. ......................... 564/281 |
| 3,692,504 | 9/1972 | Jones et al. . |
| 3,807,973 | 4/1974 | Iwama et al. . |
| 3,819,656 | 6/1974 | Barie et al. ............................ 564/281 |
| 3,819,705 | 6/1974 | Inai et al. .............................. 564/281 |
| 3,824,085 | 7/1974 | Teng et al. . |
| 3,960,514 | 6/1976 | Teng et al. . |
| 3,969,087 | 7/1976 | Saito et al. . |
| 4,156,594 | 5/1979 | Tarpley, Jr. . |
| 4,174,430 | 11/1979 | Kido et al. . |
| 4,790,961 | 12/1988 | Weiss et al. . |
| 5,108,641 | 4/1992 | Ahmed et al. ............................ 252/94 |
| 5,190,675 | 3/1993 | Gross . |
| 5,403,580 | 4/1995 | Bujanowski et al. . |

OTHER PUBLICATIONS

Y. Lin et al.; "Novel Family of Gelators of Organic Fluids and the Structure of their Gels", J. Am. Chem. Soc., 1989, 111, 5542–5551.

I. Furman et al.; "Factors Influencing the Formation of Thermally Reversible Gels Comprised of Cholesteryl 4–(2–Anthryloxy)butanoate in Hexadecane, 1–Octanol, or Their Mixtures," Langmuir, 1993, 9, 2084–2088.

R. Mukkamala and R.G. Weiss, "Anthraquinone–Steroid based Gelators of Alcohols and Alkanes", J. Chem. Soc. Chem. Commun., 1995, pp. 375–376.

T. Tachibana et al; "Chiral Mesophases of 12–Hydroxyoctadecanoic Acid jelly and in the Solid States.", Bull. Chem. Soc. Jpn., 53,, 1980, 1714–1719.

P. Terech et al.; "Small Angle Neutron Scattering Study of Steroidal Gels", J. Physique, Jun. 1985, pp. 895–903.

Primary Examiner—Jeffery T. Smith
Assistant Examiner—W C Cheng
Attorney, Agent, or Firm—Oliff & Berridge, PLC

[57] ABSTRACT

Gelators gel a variety of nonpolar and polar liquids. Moreover, gelation of various monomers with subsequent polymerization of the gelled monomers forms organic zeolites and membrane materials. An ionic gelator includes salts of compounds of the formula (I):

$$[R^1R^2R^3X\text{-}R^4]\pm Y\mp \qquad (I)$$

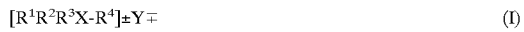

where $R^1$, $R^2$ and $R^3$ are the same or different hydrogen or organic groups including alkyl groups, alkenyl groups, alkynyl groups, aryl groups, arylalkyl groups, alkoxy groups, aryloxy groups; X is a Group IIIA or Group VA element; $R^4$ is a steroidal group, an alkyl group, an alkenyl group, an alkynyl group, an aryl group, an arylalkyl group, an alkoxy group or an aryloxy group; and Y is a Group IA or Group VIIA element or one-half of a Group IIA or VIA element, that is, a divalent counterion. The gelling agent composition may include a single isomer or mixtures of isomers of the formula (I). A non-ionic gelator also includes compounds of the formula:

$$R^1R^2R^3X \qquad (II)$$

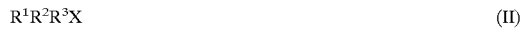

where $R^1$, $R^2$, $R^3$ and X are defined as above.

16 Claims, 3 Drawing Sheets

GELATORS

This nonprovisional application claims the benefit of U.S. Provisional Application No. 60/009,647, filed Jan. 3, 1996.

BACKGROUND OF THE INVENTION

The invention is directed to gelators and their use in gelling a plurality of nonpolar and polar liquids.

Gelation is one of the common forms of colloidal behavior, with gels having been prepared for many substances. A gel is a semisolid system having a high viscosity in the form of a jelly or paste. It is a two-phase colloidal system including a solid and a liquid in more solid form than a sol.

There are at least two general mechanisms of gel formation. The first involves the formation of a gel from an emulsoid. A fluid sol, which includes concentrated droplets of disperse phase scattered throughout a dilute solution of a dispersion medium, is cooled to a point where there is a disturbance of the equilibrium between the droplets and the surrounding dilute solution. The droplets draw the dilute solution into themselves, increase in size, and come into contact with one another forming cells like a honeycomb. This change results in a substantial decrease in fluidity of the sol, which progresses to a sponge-like structure representing a semi-solid jelly, otherwise known as a gel. Continuation of the process results in the viscous particles uniting to form a continuous phase, which encloses the droplets of what was previously the dispersion medium. The structure of the original emulsoid is thereby completely reversed with the more concentrated phase functioning as the dispersion medium, while the more dilute phase is discontinuous.

A second mechanism of gel formation involves the formation of a gel by cross-linking a polymer to form a network in a liquid medium. The liquid prevents the polymer network from collapsing into a compact mass and the network in turn retains the liquid. While some gels are cross-linked chemically by covalent bonds, other gels are cross-linked physically by weaker forces, such as hydrogen bonds and van der Waals forces.

Gelled forms of organic solvents are of particular interest, with attention currently being focused on controlling the flammability of a large variety of organic solvents in order to significantly reduce fire hazard and improve the handling characteristics of the organic solvents.

U.S. Pat. No. 2,388,887 to Weissberger et al. discloses the use of 2-alkyl-substituted 1,4-dihydroxybenzene compounds as agents for producing stiff gels with liquid aliphatic hydrocarbons and liquid halogenated aliphatic hydrocarbons.

U.S. Pat. No. 2,751,284 to Hill et al. discloses "bodying agents" for gelling normally liquid hydrocarbons and other organic liquids. The gelling agents disclosed by Hill et al., are 2-component compositions, the first liquid component comprising an aluminum alkoxide in toluene or other aromatic hydrocarbon of high solvency power, and the second liquid component comprising a mixture of a low molecular weight ketone, water, and $C_6$–$C_{18}$ fatty acids, preferably isooctanoic acids.

U.S. Pat. No. 3,084,033 to Kelly et al. discloses thickened, normally liquid hydrocarbons which are useful as fuel, as the charge in certain devices such as incendiary missiles, flame throwers, rockets, portable cooling stoves, and the like. The Kelly et al. process comprising mixing the normally liquid hydrocarbons with a very small proportion of solid, crystalline polypropylene. Surprisingly, according to Kelly et al., while propylene functions in the disclosed invention, polymers of other olefins, such as polyethylene and polybutenes were found to be completely ineffective. On the other hand, U.S. Pat. No. 3,507,635 to Sarem discloses gelled jet fuels produced by adding polyisobutylene, the resulting gel capable of being fluidized by high speed shearing, the fluidized gel then being suitable for pumping to a jet engine as a fluid.

U.S. Pat. No. 3,545,946 to Hiatt et al. discloses petroleum distillate fuel compositions in gelled form, the compositions are gelled at room temperature and liquid at elevated temperatures of about 55° C. and above. The gelled compositions comprise 75–95 weight percent of a petroleum distillate fuel and from 5 to about 25 weight percent of a paraffinic hydrocarbon gelling agent containing from about 25 to about 35 carbon atoms per molecule with a melting range of about 140° F. to about 155° F.

U.S. Pat. No. 3,692,504 to Jones et al. discloses the production of gelled compositions containing gasoline and other normally liquid hydrocarbons such as benzene, toluene, xylenes, kerosene, naphthas, and the like, the compositions gelled by a process comprising dissolving a synthetic elastomer in a normally liquid hydrocarbon and treating the resulting solution with sulfur dioxide in the presence of a suitable catalyst, i.e., typically nitrates of the alkali metals, peroxides, hydroperoxides and the like.

U.S. Pat. No. 3,807,973 to Iwama et al. discloses gelled hydrocarbon fuels prepared by gelling the hydrocarbon fuel with a fatty acid diethanolamide, diethanolamine, a fatty acid triethanolamine ester, or a triethanolamine. The compositions purportedly have the advantage that the gelled hydrocarbons are highly stable, have substantially reduced fluidity and still retain their desirable burning quality as fuels for heating means, reciprocating engines, diesel engines, jet engines and the like.

U.S. Pat. No. 3,824,085 to Teng et al. discloses esters of hydroxypropyl cellulose and hydroxypropyl starch useful as gelling agents for organic solvents, the gelling agents particularly useful in gelling methylene chloride (useful in paint stripping) and ethyl bromide (useful in soil fumigants). The hydroxypropyl cellulose laurate derivative is disclosed as particularly useful as a gelling agent for jet fuel.

U.S. Pat. No. 3,960,514 to Teng et al. discloses an improvement upon the invention of Teng et al. ('085, supra) by providing a gelled jet fuel having incorporated therein hydroxypropyl cellulose laurate and an additive comprising an elastic, high molecular weight, synthetic polymer.

U.S. Pat. No. 4,156,594 to Tarpley discloses a thixotropic gel fuel composition comprising 5 to about 75 volume percent of solid carboniferous combustible material suspended in a liquid fuel and about 1 to about 10 weight percent of a substantially completely combustible gelling agent, said combustible gelling agent selected from the group consisting of natural and synthetic gums, resins, modified castor oil polymers and the like.

Other gelling agents have been used for organic liquids as well. U.S. Pat. No. 3,969,087 to Saito et al. discloses the use of a small amount of N-acyl amino acids or derivatives thereof, such as esters, amides, and amine salts of the N-acyl amino acids, as gelling agents for nonpolar organic liquids.

U.S. Pat. No. 2,719,712 to Vaterrodt discloses the formation of gels from solvents such as hexane, heptane, octane terpenes, sesqui-terpenes, benzene, ethyl acetate, and the like, including essential oils for use in the perfume industry.

The gelling agent may be lanosterol, which is prepared by saponifying wool greases with sodium hydroxide, thereafter removing the lanoline acids as the insoluble calcium salt, and removing the lanolin alcohols by a suitable solvent such as acetone. The lanosterol is obtained from the lanolin alcohol filtrate by precipitation with acetone and methanol. The gelled hydrocarbons include 8–15% of lanosterol.

Terech, P. et al., J. Physique 46: 895–903 (1985) describes the results of a Small Angle Neutron Scattering (SANS) study of a gel formed by a dilute solution (less than one weight percent solution) of a paramagnetic modified steroid, 3-beta-hydroxy-17,17-dipropenyl-17a-aza-D-homoandrostanyl-17a-oxy in cyclohexane.

Tachibana, T. et al., Bull. Chem. Soc. Jpn. 53: 1714–1719 (1980), describes optically active 12-hydroxyoctadecanoic acids which form thermally reversible gels with aromatic solvents or carbon tetrachloride.

U.S. Pat. No. 4,790,961 to Weiss et al. describes a thermally reversible gel and a method for the formation of gels of certain organic liquids by adding to the organic liquid a gelling agent which is a cholesteryl and cholestanyl ester of anthracene and anthraquinone analogs and derivatives thereof. The mixture is heated until homogeneous and upon cooling a gel is formed. U.S. Pat. No. 5,403,580 to Bujanowski et al. utilize the same or similar gelator as described in U.S. Pat. No. 4,790,961 for gelling organosilicon compounds. The gelation of organosilicon compounds is also mentioned in the patent to Weiss et al. The subject matter of these patents is incorporated herein by reference.

In an article by Lin et al., J. of Amer. Chem. Soc., Vol. 111, No. 15, pp. 5542–51, 1989, cholesteryl 4-(2-anthryloxy) butanoate and related molecules are described as a gelator for organic fluids. These gelators possess a butanoate linking group between the steroidal group in the anthryloxy group. See also Furman et al., Langmuir, Vol. 9, No. 8, pp. 84–88, 1993, and Mukkamala, J. Chem. Soc., Chem. Commun., pp. 375–6, 1995, which also disclose similar gelators.

U.S. Pat. No. 4,174,430 to Kido et al. describes a process for producing porous polystyrene gel by suspension polymerization in an aqueous system. More than 5 mol. % of a radical polymerization catalyst is added to styrene and divinyl benzene in an inert organic solvent. The organo solvent provides the porous nature of the material, which is formed by cross-linking the styrene with divinyl benzene. The porous polystyrene gel is used as a filler for chromatography.

However, in spite of the substantial research conducted in an effort to develop gelled organic solvents, a need has continued to exist for a gelator capable of gelling a wide variety of polar and nonpolar liquids. Moreover, there is a need for highly stable gelled material that is nontoxic and that may be fabricated into a membrane material for filtration purposes and an organic zeolite for control release of various compounds such as medicaments.

SUMMARY OF THE INVENTION

The present invention is directed to gelators that gel a variety of nonpolar and polar liquids. Moreover, the present invention is related to the gelation of various monomers with subsequent polymerization of the gelled monomers to form organic zeolites and membrane materials.

The gelators of the present invention comprise (A) compounds of the general formula (I):

$$[R^1R^2R^3X-R^4]^+Y^= \qquad (I)$$

where $R^1$, $R^2$ and $R^3$ are the same or different hydrogen or organic groups including alkyl groups, alkenyl groups, alkynyl groups, aryl groups, arylalkyl groups, alkoxy groups, aryloxy groups; X is a Group IIIA or Group VA element; $R^4$ is a steroidal group, an alkyl group, an alkenyl group, an alkynyl group, an aryl group, an arylalkyl group, an alkoxy group or an aryloxy group; and Y is a Group IA or Group VIIA element or one-half of a Group IIA or VIA element (that is, a divalent counterion); and (B) compounds of the formula (II):

$$R^1R^2R^3X \qquad (II)$$

where $R^1$, $R^2$, $R^3$ and X are defined as above. The gelling agent composition may include a single isomer or mixtures of isomers of the formula (I) and (II).

DESCRIPTION OF PREFERRED EMBODIMENTS

Figure 1:
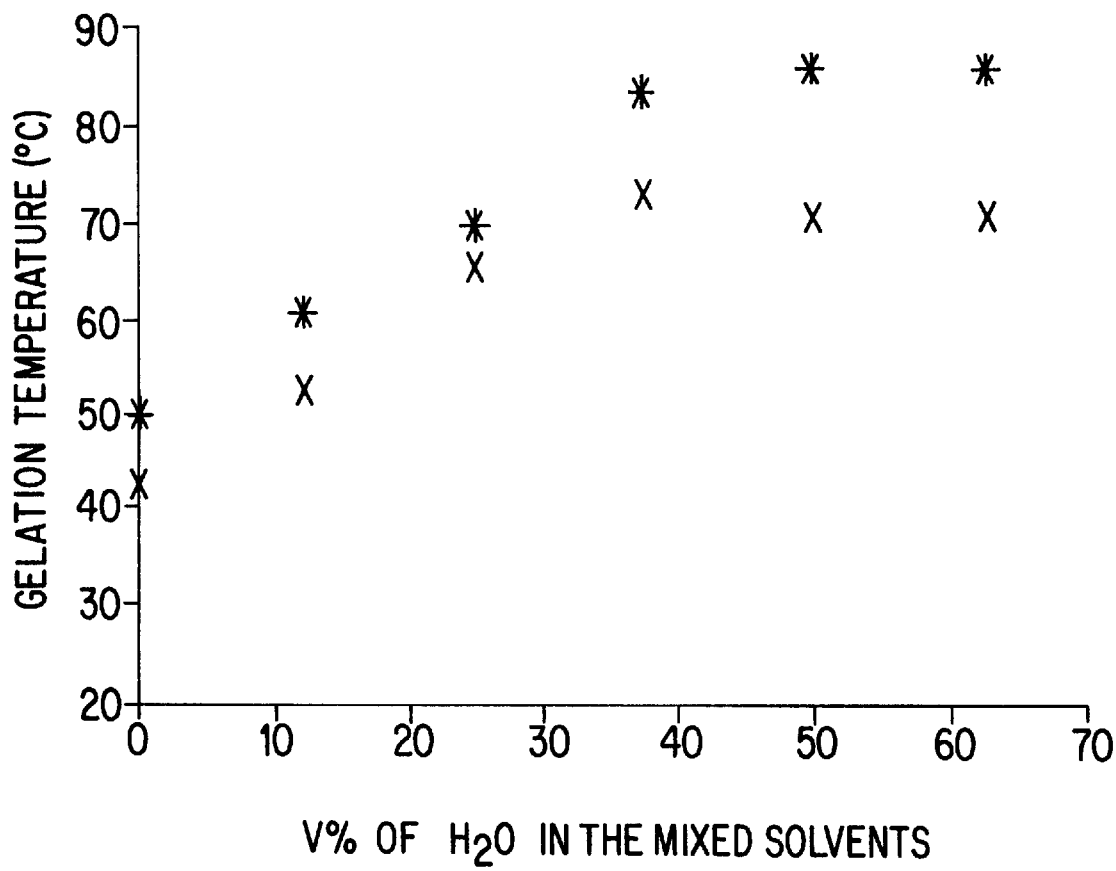
FIG. 1 demonstrates the effect of gel liquid polarity and gelator solubility on the gelling capability or gelation temperature for gels composed of 0.98 wt. % of gelators β-2(designated as *), formula (VI), and α-2(designated as x), formula (VII), in water/1-propanol mixtures as the volume percentage of water increases.
Figure 2:
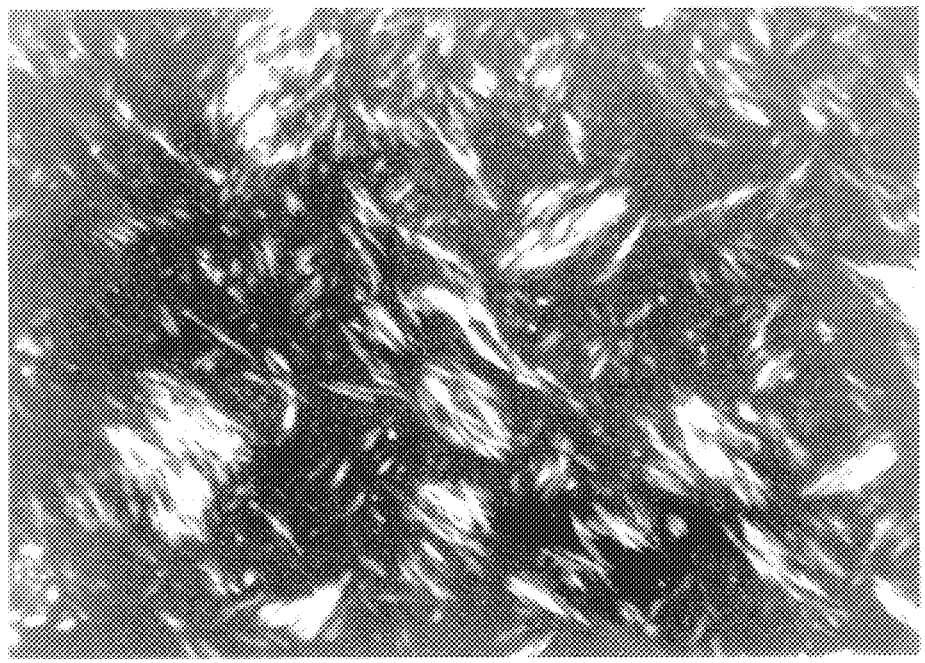
FIG. 2 is an optical micrograph (X175) between crossed polars of the gel phase of 6.0 wt % of N-dodecyl-N,N,N-trioctadecylammonium iodide in n-dodecane at room temperature.

Surfactants in aqueous media are known to form many types of aggregates, including lyotropic liquid crystals, vesicles and micelles. According to the present invention, it has been discovered that certain surfactants unexpectedly provide stable gels in a variety of nonpolar and polar liquids. Certain gelators, such as trialkylcholestanyl ammonium salts, gel a variety of nonpolar and polar liquids in a thermally reversible fashion.

The term "nonpolar liquids" includes organic liquids including petroleum hydrocarbons such as gasoline, naphthas, kerosene, gas oil, heavy oil, and crude oil; lubricating oils such as spindle oil and turbine oil; liquid paraffin; pure hydrocarbons such as xylene, alkanes having one to thirty carbon atoms, e.g., hexane, heptane, octane, decane, tetradecane and hexadecane; cyclohexanes such as decalin and chlorohexane; alkenes having one to thirty carbon atoms such as 1-tetradecene and 1,3-penta diene; aldehydes such as anisaldehyde and heptanal; phosphoric esters, such as tributyl phosphate and tricresyl phosphate; normally liquid polyoxyalkylene monoalkyl ethers such as polyoxyethylenemonolauryl ether containing four to six oxyethylene units, polyoxypropylene mono $C_4$–$C_{12}$ alkyl ether containing 10–50 oxypropylene units; normally liquid polyoxypropylenemonolauryl ether; normally liquid polyoxyalkylene glycol fatty acid esters such as polyoxyethylene glycol lauric or oleic acid esters containing four to six oxyalkylene units;

fatty oils such as corn oil, soybean oil, olive oil, rape seed oil, cotton seed oil, sardine oil, herring oil and whale oil; silicone oil; and mixtures thereof.

The term "polar liquids" includes liquids having molecules in which ionization is possible in acidic or basic aqueous media such as water, sulfoxides such as dimethyl sulfoxides, alkanols having one to twenty carbon atoms such as 1-propanol, 1-octanol, 1-dodecanol, and 4-heptanol; benzyl alcohol; esters such as n-pentyl acetate, butyl acetate, amyl acetate, diethyl phthalate, dibutyl phthalate, dioctyl phthalate, diethyl sebacate and dioctyl sebacate; alkanoic acids such as nonanoic acid; and amines such as n-butylamine, benzylamine, N-methylamine, and alpha-methyl benzylamine.

In the general formulae (I) and (II) above, $R^1$, $R^2$, $R^3$ and $R^4$ represent the same or different substituents and are organic radicals that may be substituted or unsubstituted and may be straight chained, branched or cyclic, saturated, unsaturated or aromatic. Examples of such organic radicals include $C_1$–$C_{30}$ alkyl radicals; $C_2$–$C_{30}$ alkenyl radicals; $C_2$–$C_{30}$ alkynyl radicals; $C_3$–$C_{30}$ cycloaliphatic radicals; aryl radicals such as phenyl, naphthalene, phenanthrene, anthracene; and aralkyl radicals such as benzyl, methylbenzyl and phenylethyl. These radicals may be unsubstituted or substituted with substituents such as halogen (e.g., chloro-, fluoro-, iodo-, and bromo-substituted hydrocarbons) and oxygen substituents (e.g., oxy-, alkoxy- or hydroxy-substituted hydrocarbons). Preferred organic radicals are alkyl, alkenyl and alkynyl radicals having from 1 to about 20 carbon atoms. More preferably, the organic radicals are alkyl, alkenyl and alkynyl radicals having from 1 to 18 carbon atoms.

Gelation may be promoted and gel stability may be enhanced by the ionic interactions available among ionic surfactant molecules. For example, gelators having organic radicals ($R^1$, $R^2$ and $R^3$) with one or more long alkyl chains gel a wide variety of polar and nonpolar liquids. Accordingly, it is preferred that at least one of $R^1$, $R^2$ and $R^3$ represents an alkyl, alkenyl or alkynyl radical having at least 10 carbon atoms, preferably at least 12 carbon atoms, and more preferably at least 15 carbons atoms.

In formulae (I) and (II) above, when X represents a Group VA element (N, P, As, Sb or Bi), Y preferably represents a Group VIIA element (F, Cl, Br, I) and when X represents a Group IIIA element (B, Al, Ga, In or Tl), Y preferably represents a Group IA element (Li, Na, K, Rb, Cs). Preferably, the linkage group X is a Group VA element and Y is a Group VIIA element and, more preferably, the linkage group X is nitrogen and the Y group is iodide.

The linkage group X may be trivalent or tetravalent and may possess a negative or positive charge or be neutral (e.g., trivalent and lacking Y). Accordingly, the gelator may be cationic or anionic with negatively charged counterions ($F^-$, $Cl^-$, $Br^-$ and $I^-$) or anionic with positively charged counterions ($Li^+$, $Na^+$, $K^+$, $Cs^+$ or $Rb^+$).

The selection of particular counterions that form the salts of formula (I) may depend upon the nature of the liquid that is being gelled. Normally, cationic surfactants with chloride counterions aggregate in aqueous media at higher concentrations than those with bromide or iodide counterions. In nonpolar solvents, the opposite trend applies. Accordingly, when utilizing cationic gelators, it is preferable to utilize bromide or iodide counterions, and more preferably, iodide counterions.

In formula (I), $R^4$ may also represent a steroidal group such as a cholesteryl group, a cholestanyl group or their derivatives. The cholesteryl group may be represented by the formula (IIIA):

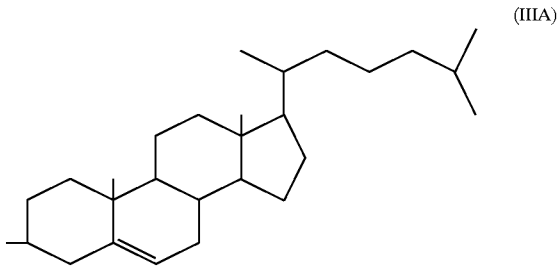

(IIIA)

The cholestanyl group may be represented by the formula (IIIB):

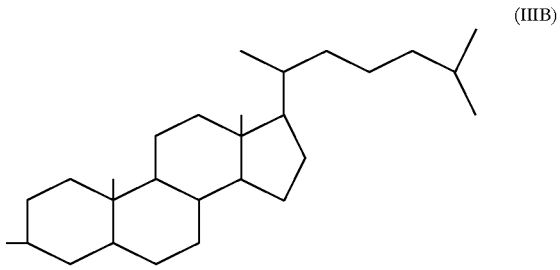

(IIIB)

By "derivative" is intended the parent molecular skeletons of cholesteryl and cholestanyl in which one or more hydrogen atoms have been removed or have been replaced (substituted) by other atoms or groups of atoms (e.g., —halogen, —$NH_2$, —O, —OH, —SH, —$CO_2H$. —CHO, —R (where R is a simple or complex group of atoms for which the atom linked to the parent molecular skeleton is carbon), —$CO_2R$, —SR, OR, —NHR, —$N(R)_2$, or the like).

A variety of gelator compounds of the above formula (I) may provide suitable gelating activity, depending on the number and length of alkyl chains in the gelator, the isomeric structure of the gelator, the charge on the gelator, the nature of the counterion, the gel liquid polarity and the gelator solubility in the gel liquid.

Suitable ionic gelators that gel nonpolar and polar liquids in a thermally reversible fashion include the following compounds:

A. N-(3β-cholestanyl)-N,N-dimethyl-N-octadecylammonium iodide of the formula(IV):

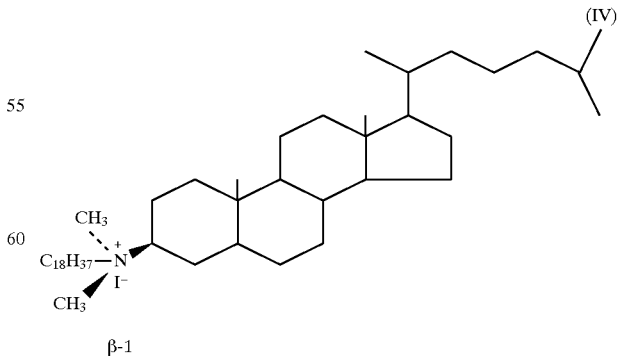

(IV)

β-1

B. N-(3α-cholestanyl)-N,N-dimethyl-N-octadecylammonium iodide of the formula (V):

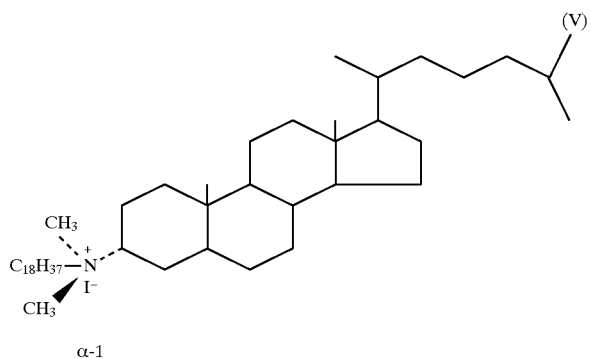

α-1

C. N-(3β-cholestanyl)-N-methyl-N,N-dioctadecylammonium iodide of the formula (VI):

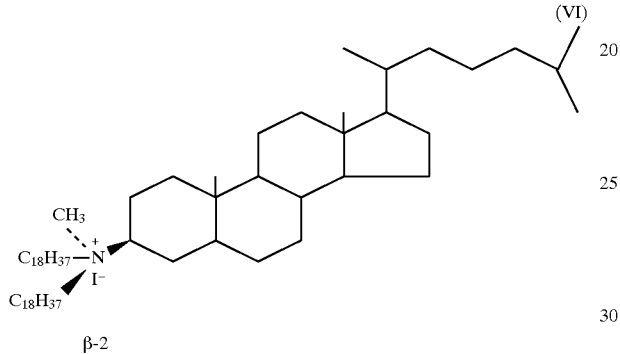

β-2

D. N-(3α-cholestanyl)-N-methyl-N,N-dioctadecylammonium iodide of the formula (VII):

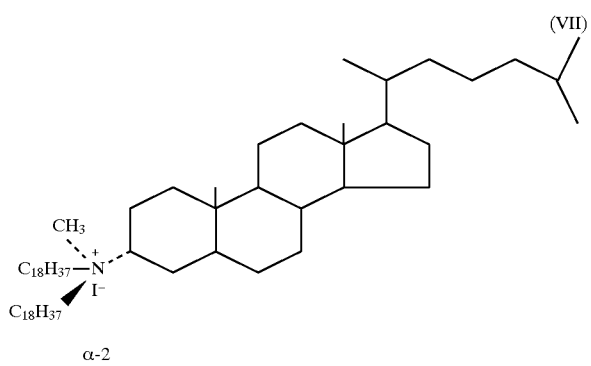

α-2

E. N-(3β-cholestanyl)-N-methyl-N,N-dioctadecylammonium chloride of the formula (VIII):

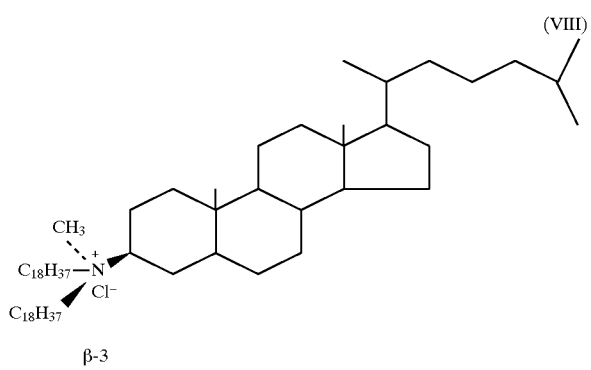

β-3

F. N-methyl-N,N,N,-trioctadecylammonium iodide of the formula (IX):

G. N-dodecyl-N,N,N-trioctadecylammonium iodide of the formula (X):

H. N,N,N,N-tetraoctadecylammonium iodide of the formula (XI):

I. N-benzyl-N,N,N-trioctadecylammonium bromide of the formula (XII):

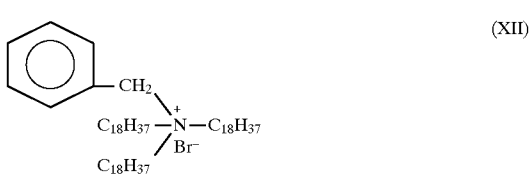

Other suitable gelators include N-ethyl-N,N,N-trioctadecylammonium iodide, N-propyl-N,N,N-trioctadecylammonium iodide, N-butyl-N,N,N-trioctadecylammonium iodide, N,N,N,N-tetraoctadecylammonium bromide, trioctadecylammonium iodide, trioctadecylammonium chloride, N,N,N,N-tetradodecylammonium iodide and derivatives thereof.

Of these, a preferred ionic gelator is the gelator represented by formula (VI).

Additional gelators of the present invention that provide thermally reversible organic liquid gels include, for example, compounds of the general formula:

wherein $R^1$, $R^2$, $R^3$ and X are as defined above.

Suitable gelators include tertiary amines such as trioctadecylamine (TOA), methyldioctadecylamine, or the α- or β-anomer of cholestanyldioctadecylamine (CDA), related compounds or derivatives thereof.

When tertiary amines, such as trioctadecylamine (TOA) or the α- or β-anomer of cholestanyldioctadecylamine (CDA) are dissolved by heating in an organic liquid and then cooled, viscoelastic, thermally-reversible gels form in which the amines aggregate in long, thin, interlocking crystalline strands as shown in FIG. 1. The liquid component remains isotropic, but is immobilized by surface tension. Although there is precedence for gelation of organic liquids by amides, this behavior appears to be unprecedented for simple, low molecular weight amines and ammonium salts, even when they are dimeric or trimeric. This indicates that factors different from those governing the aggregation of salts in aqueous media are operative.

The gels of the present invention may be prepared simply, for example, by homogeneously admixing a gelling agent having the above formulae (I) or (II) with polar or nonpolar liquid under conditions sufficient to effect dissolution, usually by heating, and subsequently allowing the solution to gel, usually by cooling. Homogeneous admixing of the reactants may be conducted at temperatures ranging from room temperature or below, to the boiling point of the liquid. The gelling agent may be added in the form of powder particles or as a solution dissolved in a suitable solvent, typically the liquid being gelled, or other suitable solvents including polar solvents such as the polar liquids listed above, and nonpolar solvents such as the nonpolar liquids listed above. The gels of the present invention may also be formed, for example, by dissolving the gelling agent in the liquid at elevated temperatures, and thereafter cooling the resulting solution to a lower temperature, whereby gel formation occurs while standing.

According to the present invention, the gelling agent may be employed generally in a wide range. Preferred is a range of about 0.05% to 20% by weight based upon the liquid to be gelled, more preferably 0.075 to 10%, and even more preferably 0.1 to 1.5 or 2.0%. The firmness of the resulting gel may be controlled depending on the kind and amount of gelling agent added. A suitable amount of gelling agent may be readily determined by routine experimentation and will vary with the desired physical property of the gel and other components therein. As is understood by those skilled in the art, a lower amount of gelling agent often makes the composition more desirable, inasmuch as the gelling agent may often demonstrate chemical and physical properties which differ from the end use properties of the gelled liquids. Accordingly, it is often desirable to minimize the amount of gelling agent required.

More than one gelator maybe utilized to gel a particular liquid. For example, a mixture of two different isomers or homologues of a particular gelator compound or a mixture of more than one gelator compound (e.g., different linkages, different counterions, different organic substituents, etc.) may be used.

When preparing gels in accordance with the process of this invention, the requisite amount of gelling agent is admixed with the liquid and the materials are blended, for example under ambient conditions of temperature and pressure. Different temperatures and pressures may be utilized in the mixing process where, for example, loss of vapors, in the case of a low-boiling liquid hydrocarbon, is to be avoided (use lower temperatures and/or higher pressures) or when easier mixing, in the case of higher-boiling liquids, is to be obtained (use higher temperatures and/or lower pressures).

The components may be mixed by any means such as stirring, shaking, or passing the mixture through a homogenizer to produce a homogeneous composition. Regardless of the method of blending, gels are produced as a result of obtaining an intimate dispersion of the gelling agent in the liquid.

The liquid of the present invention, once gelled, varies in viscosity from a thin, pourable type to a shape retaining gel. The resulting gels are highly cohesive, stable in storage for variable periods (depending upon the gelling agent, its concentration, the liquid, and the temperature of storage), thermally reversible, and are sheer stress thinnable.

The practice of the present invention is particularly well suited for use in the fuel industry. In the practical use of fuel, it is frequently desirable to store fuel in a solid form. This is especially true in the case of aviation jet fuel. The rupturing of fuel tanks in jet aircraft in crashes during landing and takeoff and the resulting spreading of the highly flammable fuel is a problem of substantial proportions. Further, fuel vaporizes easily and the fuel vapors are readily ignited by hot engine parts or sparks from metal impact. On the contrary, when fuels are gelled, the degree of vaporization and the extent to which the fuel is scattered upon impact are substantially decreased, with concomitant decrease in the danger of rapid, spreading fire or explosion.

Gelling agents for liquids are also useful for facilitating the removal or recovery as a result of unintentional spills. In like manner, gelling agents may be added to tanks which have developed leaks or holes, thereby preventing further loss of the tank contents.

Additionally, the gelling agents may be used in the preparation of paints; inks; lubricants and greases, such as silicone based greases; oil-type cosmetics, such as topical creams, shampoos, deodorants, etc.; napalm-type incendiaries; display devices, such as electro-optical switching screens television screens, etc.; and films, such as X-ray and visible photographic films, heat sensitive films, information storage devices, and the like; pharmaceuticals; time-released substances, including organic zeolites; filter membranes; and other liquid materials that are utilized in gel form.

The gelators of the present invention may also be utilized to form irreversible gels of monomer liquids for subsequent fabrication of separation membranes and "organic zeolites" (that is, polymeric structures with hollowed channels). Suitable gelators for this application include gelators of formula (I) above in which at least one of $R^1$, $R^2$, $R^3$ and $R^4$ have from 1 to 30 carbon atoms. Preferably, at least one of $R^1$, $R^2$, $R^3$ and $R^4$ have more than 10 carbon atoms, and more preferably, more than 15 carbon atoms. Additionally, it is more preferable that more than one of $R^1$, $R^2$, $R^3$ and $R^4$ have over 15 carbon atoms.

Although any Group III and Group V linkage X may be employed in formulae (I) and (II), preferably a cationic linkage, such as a linkage through a nitrogen atom, is utilized. As mentioned above, any suitable negatively charged counterion may be utilized, with a halogen, e.g., iodine, being a preferred counterion.

The separation membranes and organic zeolites of the present invention may be fabricated, for example, by preparing gels of monomeric material with subsequent polymerization thereof. A free-radical polymerization initiator having similar polarity and solubility as the gel monomer may be incorporated into the gel. Additionally, a cross-linking agent of similar polarity and solubility of the gel monomer may also be incorporated into the gel before or after gelation. Preferably, a photochemical free-radical initiator that is stable at high temperatures (e.g., greater 100° C.) is utilized. Polymerization of the gel is initiated by radiation that can be absorbed by the initiator. Alternatively, polymerization may be initiated by photoinduced electron transfer from the counterion to the monomer or cross-linking agent or by gamma radiation in the absence of an additional initiator. Additives may be added before or after gelation, but are preferably added before gelation.

The polymerized gel may then be heated to a temperature below the glass transition temperature of the cross-linked polymer in a solvent that is capable of dissolving the gelator without appreciably swelling the polymer. Once the gelator is removed, a porous structure will remain with numerous channels. The cross-sectional diameters in embodiments of the channels, because they are formed by strands of the gelator, will be of the same size as the strands that are removed. The cross-sectional diameters in embodiments will range from about 10 to about 100 nanometers, depending upon the gelator utilized, the number and length of alkyl chains on the gelator, the charge on the gelator, the nature of the counterion and the liquid polarity (gelator solubility) of the monomer liquid gelled.

To form membrane material, sections of the polymerized material may be cut or sliced from the material prior to removing the gelator to provide wafers or substrates. Mesoporous membranes will remain after the gelator is subsequently removed. If the gelator is removed from the polymer material without sections being removed, a material similar to a zeolite with an organic framework will remain.

The vacated channels of both the organic zeolite and the membrane material may be filled with a variety of compounds (e.g., drugs and medicaments) for controlled release of the compounds. Additionally, the membranes may be utilized for the separation of large proteins or enzymes on the basis of size by filtration or gel-type chromatography.

Suitable monomers that may be gelled according to the present invention include ethylenically substituted monomers, condensation monomers such as caprolactam, ethylenically unsaturated monomers such as styrene, acrylonitrile, alkyl methacrylates such as methyl methacrylates, or derivatives of these monomers. Preferably, the monomer to be gelled is styrene or methylmethacrylate. The monomer may be used in an amount ranging from about 80 to about 99.9 wt. %, preferably from about 90 to about 99 wt. %, and more preferably from about 95 to about 98 wt. % based on the total amount of monomer and cross-linking agent.

Suitable cross-linking agents according to the present invention include α,ω-alkanedithiols, divinylbenzene, or diethynylbenzene or other diethylenically or triethylenically substituted compounds whose structures mimic the monomer. Preferably, the cross-linking agent is divinylbenzene for styrene. The cross-linking agent may be used in an amount ranging from about 1 to about 50 wt. %, preferably from about 5 to about 40 wt. %, and more preferably from about 5 to about 20 wt. % based on the total amount of monomer and cross-linking agent.

Suitable photochemical free-radical initiators according to the present invention include benzoin alkyl ethers; azoalkylnitriles such as azoisobutyronitrile or azobisdimethylvaleronitrile; benzoyl peroxide; or the derivatives of these compounds. The initiators may be used in an amount ranging from about 10 to about 0.1 wt. %, preferably from about 8 to about 0.5 wt. %, and more preferably from about 5 to about 1 wt. % based on the total amount of monomer and cross-linking agent.

The gelator may be incorporated into the mixture in amounts as designated above. Suitable gelling agents include those provided by formulae (I) and (II) and, preferably those of Examples I–IX, and more preferably those of Examples VI–IX.

Additionally, gelation may be conducted in the presence of organic solvents and/or aqueous media. The organic solvents must be miscible to both the monomer and the cross-linking agent. Suitable organic solvents include aromatic hydrocarbons such as toluene and benzene, aliphatic esters such as ethyl acetate and butyl acetate, saturated aliphatic hydrocarbons such as nonane and dodecane, alcohols such as n-amyl alcohol and isoamyl alcohol and nitrocompounds such as nitromethane and nitroethane. The organic solvent or mixture of the organic solvent may be used in an amount ranging from about 50 to about 250% by weight, preferably from about 70 to about 200% by weight, and more preferably from about 100 to about 150% by weight based on the total amount of monomer and cross-linking agent.

Having now generally described the invention, a further understanding may be obtained by reference to certain specific examples which are provided herein for purposes of illustration.

EXAMPLES

The gelators of Examples I–V are synthesized by the following procedure. N-cholestanyl-octadecanamine diastereomers are first prepared by the following process. To a stirred solution of 4.2 g (15.6 mmol) octadecylamine (Aldrich) in 90 ml of anhydrous methanol (Aldrich) is added 2.0 ml (10 mmol) of 5N HCl-MeOH, followed by 3.0 g (7.8 mmol) 5α-cholestan-3-one and 0.33 g (5.2 mmol) $NaBH_3CN$ (Aldrich). The reaction is conducted in a stoppered round-bottomed flask at room temperature for 48 h. The mixture develops white precipitation. The solid is collected by filtration and then taken up in 150 ml $CHCl_3$ and washed with three portions of 50 ml water. Finally, the organic layer is dried over $MgSO_4$ (anhydrous) and evaporated down to a solid (4.8 g, 96%); purification by silica column (5%, then 10% ethyl acetate/hexane) gives 2.3 g (46%) first diasteromer (β at C3) and 1.1 g (22%) second diasteromer (α at C3). For the β isomer, its mp is 76°–77° C. FT-IR (KBr pellet $cm^{-1}$): 2924, 2850 (cholestanyl, octadecyl, C-H vvs), 1472, 1387 (C-H bending). $^1$HNMR (270 MHz, $CDCl_3$/TMS,ppm): 2.62–2.57 ($CH_2$, t, J=7.03 Hz, 2H), 2.50–2.35 (CH, broad, m, 1H), 2.0–0.64 (cholestanyl, octadecyl groups, m, 108H). MS(CI) m/e calcd for $C_{45}H_{86}N$ [$(M+H)^+$] 641, found 641.

For the α isomer, its mp is 50°–52° C. FT-IR (KBr pellet $cm^{-1}$): 2913, 2850 (cholestanyl, octadecyl, C-H vvs), 1461, 1385 (C-H bending. $^2$HNMR (270 MHz, $CDCl_3$/TMS, ppm): 2.79 (CH, sharp, m, 1H), 2.55–2.50 ($CH_2$, t, J=7.03 Hz, 2H), 2.0–0.64 (cholestanyl, octadecyl groups, m, 108H). MS(CI) m/e calcd for $C_{45}H_{86}N$ [$(M+H)^+$] 641, found 641.

Subsequently, N-cholestanyl-N-octadecyl-octadecanamide is prepared by the following process. 1.8 g (2.8 mmol) N-cholestanyl-octadecanamine, 8 ml distilled benzene, 0.2 ml dried pyridine are added into a 50 ml round-bottomed flask. The amidation is started by adding 1.6 ml (4.7 mmol) freshly prepared stearoyl chloride under dry atmosphere with stirring at room temperature. The reaction is continued at 35° C. for 4 h. The reaction mixture is taken up in 150 ml benzene, washed with $H_2O$ twice. The organic layer is dried ($MgSO_4$) and evaporated under vacuum to a solid which is dissolved and stirred in 50 ml 1:1 mix of THF-$Na_2CO_3$ aqueous solution at 40° C. fpr 2 h. Then THF is removed under vacuum. 1.5 g (59%) solid is obtained by extracting the product with 500 ml 1:2 hexane/benzene, drying over $MgSO_4$ (anhyd) and evaporating the solvents under vacuum. Recrystallization in acetone/$CH_2Cl_2$ gives 1.3 g (51%) white product, mp 58°–60° C. FT-IR (KBr pellet $cm^{-1}$): 2928, 2863 (cholestanyl, octadecyl C-H vvs), 1644 (C=O, s), 1463, 1388 (C-H bending). $^1$HNMR (270 MHz, $CDCl_3$/TMS, ppm): 3.2–3.05 ($CH_2$, m, 2H), 2.45–2.20 ($CH_2$, m, 2H), 2.0–0.65 (cholestanyl, octadecyl groups, 131H). MS (CI) m/e calcd for $C_{63}H_{120}NO$ [$(M+H)^+$] 907, found 907.

N-cholestanyl-N,N-dioctadecanamine is then prepared by the following process. 0.1 g (2.6 mmol) $LiAlH_4$ (Aldrich), 5 ml dried THF (prepared by distilling over $LiAlH_4$) are added into a 25 ml round-bottomed flask. Then 10 ml dried THF solution of 1.0 g (1.1 mmol) N-cholestanyl-N-octadecyl-octadecanamide is added into the reaction mixture under vigorous stirring. The mixture is refluxed for 15 hours. The solid residue is taken up in 200 ml hexane upon removal of THF solvent. Then the organic layer is washed with diluted NaOH, $H_2O$, and dried over $K_2CO_3$, finally evaporated under vacuum. 0.55 g (56%) white solid is obtained after running silica column (8% ethyl acetate/hexane, Rf=0.13 visualized in an iodine chamber.), mp 63°–66° C., FT-IR (KBr pellet $cm^{-1}$): 2918, 2849 (cholestanyl, octadecyl, C-H vvs), 1470, 1385 (C-H bending). $^1$HNMR (270 MHz, $CDCl_3$/TMS, ppm): 2.56–2.33 ($CH_2$, CH, m, 5H), 2.0–0.65 (cholestanyl, octadecyl groups, m, 130 H). MS(CI) m/e calcd for $C_{63}H_{122}N$ [$(M+H)^+$] 893, found 893.

The above product is utilized to prepare N-cholestanyl-N,N-dioctadecyl-N-methylammonium iodide by the following process. 0.15 g (0.17 mmol) N-cholestanyl-N,N-dioctacanamine, 7 ml anhydrous ethanol and 0.05 ml (0.83 mmol) $CH_3I$ are added into a round-bottomed flask under $N_2$ atmosphere and with vigorous stirring. The mixture is stirred at 45°–60° C. for 14 h. When cooled to room temperature, the mixture forms a gel phase. A yellowish solid is obtained after the gel is broken by stirring, and filtering. 0.07 g (40%) product is recovered by recrystallizing twice in ethanol. It shows interesting fan-like textures at 166°–177° C. and melts at 177°–179° C. FT-IR (KBr pellet $cm^{-1}$): 2920, 2851 (cholestanyl, octadecyl, C-H vvs), 1471, 1384 (C-H bending). $^1$HNMR (270 MHz, $CDCl_3$/TMS, ppm): 3.60–3.45 (CH, m, 1H), 3.43–3.325 ($CH_2$, m, 4H), 3.22–3.16 ($CH_3$, s, 3H), 2.10–0.65 (cholestanyl, octadecyl groups, m).

Example I

A. N-(3β-cholestanyl)-N,N-dimethyl-N-octadecylammonium iodide of the formula(IV):

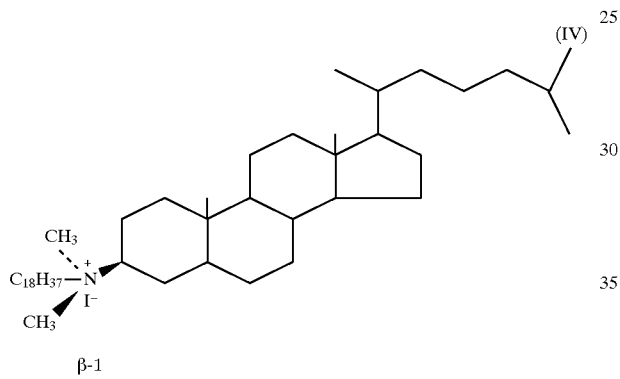

β-1

Example II

B. N-(3α-cholestanyl)-N,N-dimethyl-N-octadecylammonium iodide of the formula (V):

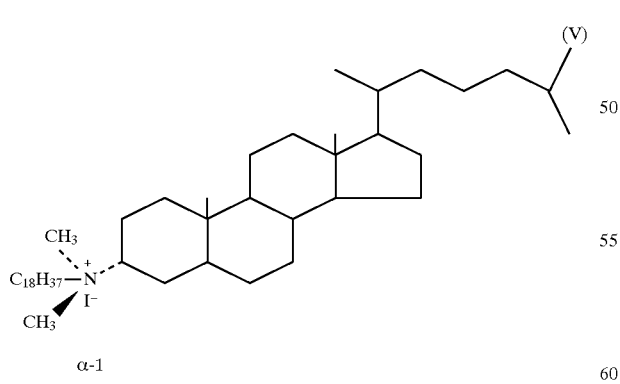

α-1

Example III

C. N-(3β-cholestanyl)-N-methyl-N,N-dioctadecylammonium iodide of the formula (VI):

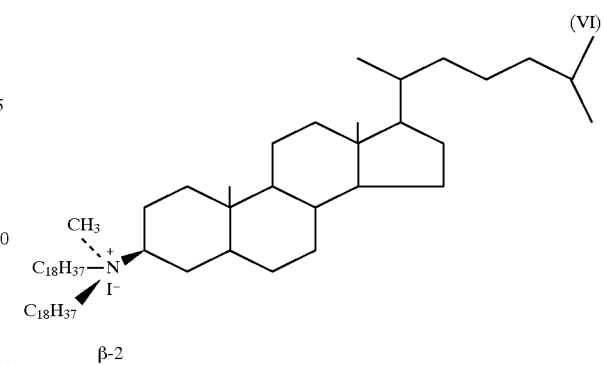

β-2

Example IV

D. N-(3α-cholestanyl)-N-methyl-N,N-dioctadecylammonium iodide of the formula (VII):

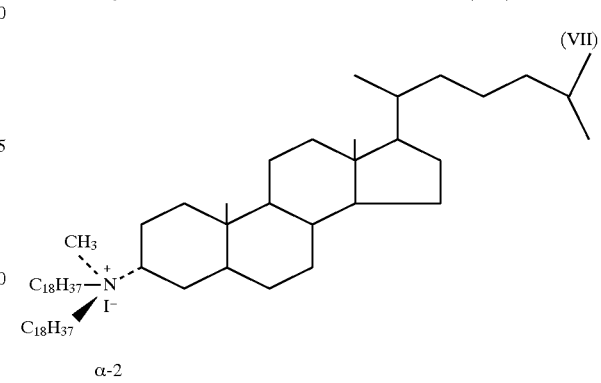

α-2

Example V

E. N-(3β-cholestanyl)-N-methyl-N,N-dioctadecylammonium chloride of the formula (VIII):

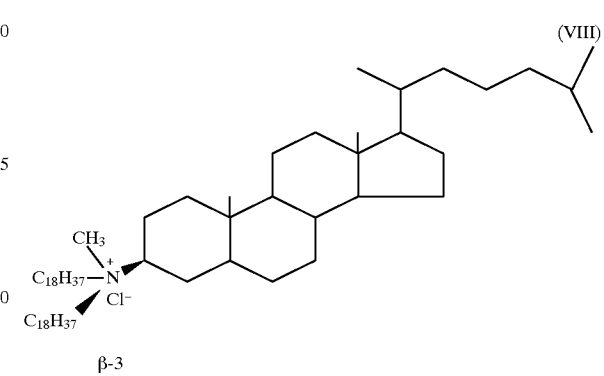

β-3

The gelators of Examples VI–IX are synthesized by the following procedures. N-methyl-N,N,N-trioctadecylammonium iodide is prepared according to the following process. 0.10 g (0.13 mmol) trioctadecylamine is dissolved in 1.5 ml THF (certified grade, Fisher), and 0.1 ml (1.6 mmol) $CH_3I$ (99%, Aldrich) is placed in the above solution. The solution is stirred in a nitrogen atmosphere at 38°–40° C. for 3 h. 95 mg (80%) white solid, mp 108°–111° C., is obtained after the solvent is evaporated under house vacuum pressure, and the residue is recrystallized in ethanol (anhydrous). IR (KBr) 2917, 2859 (C-H stretching, vvs), 1473 (C-H bending, w) $cm^{-1}$. $^1$HNMR ($CDCl_3$) δ 3.52–3.38 ($CH_2$, m, 6H), 3.31 ($CH_3$, s, 3H), 1.76–0.82 (heptadecyl groups, m, 105H).

N-dodecyl-N,N,N-trioctadecylammonium iodide is prepared according to the following process. 0.14 g (0.18 mmol) trioctadecylamine, 0.20 ml (0.8 mmol) $C_{12}H_{25}I$ (99%, Aldrich), and 4 ml butanone (ACS, Baker) are placed into a dry nitrogen atmosphere with stirring for 4 days. 85 mg (44%) white solid, mp 93°–94° C., is obtained after the solvent is evaporated, and the residue is recrystallized twice in ethanol (anhydrous). IR(KBr) 2920, 2857 (C-H stretching, vvs), 1473, 1381 (C-H bending, w) $cm^{-1}$. $^1$HNMR (CDCl$_3$) δ 3.65–2.99 (CH$_2$, m, 8H), 1.91–0.49 (heptadecyl and undecyl groups, m, 134H).

Tetraoctadecylammonium iodide is prepared according to the following process. 70 mg (0.090 mmol) trioctadecylamine, 0.10 g (0.26 mmol) octadecyl iodide (recrystallized from 95% material, Fluka), and 3 ml CH$_3$CN (HPLC grade, Fisher) are placed into a 10 ml roundbottomed flask. The mixture is refluxed under a dry nitrogen atmosphere with stirring for 5 days. 55 mg (53%) white solid, mp 104°–105° C., is recovered after the solvent is evaporated, and recrystallized twice in ethanol/Et$_2$O. IR(KBr) 2918, 2855 (C-H stretching, vvs), 1471, 1386(C-H bending, w) $cm^{-1}$. $^1$HNMR(CDCl$_3$) δ 3.48–3.16(CH$_2$, m, 8H), 1.78–0.81 (heptadecyl groups, m, 148H).

N-benzyl-N,N,N-trioctadecylammonium bromide is prepared according to the following process. 0.10 g (0.13 mmol) trioctadecylamine, 0.30 ml (2.5 mmol) benzyl bromide (98%, Aldrich), and 3 ml THF (certified grade, Fisher) are placed into a 10 ml round-bottomed flask. The mixture is refluxed under a dry nitrogen atmosphere with stirring for 1 day. 80 mg (65%) white solid, mp 82°–83° C., is recovered after the solvent is evaporated, and the residue is recrystallized twice in a mix of hexane and ether. IR(KBr) 2916, 2851 (C-H stretching, vvs), 1473, 1386(C-H bending, w) $cm^{-1}$. $^1$HNMR(CDCl$_3$) δ 7.74–7.36 (aromatic H, m, 4H), 5.19–4.76 (CH2,s, 2H), 3.69–3.12(CH$_2$, m, 6H), 2.05–0.67 (heptadecyl groups, m, 104H).

Example VI

F. N-methyl-N,N,N,-trioctadecylammonium iodide of the formula (IX):

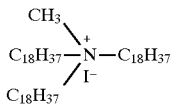

(IX)

Example VII

G. N-dodecyl-N,N,N-trioctadecylammonium iodide of the formula (X):

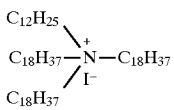

(X)

Example VIII

H. N,N,N,N-tetraoctadecylammonium iodide of the formula (XI):

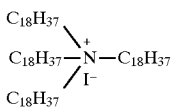

(XI)

Example IX

I. N-benzyl-N,N,N-trioctadecylammonium bromide of the formula (XII):

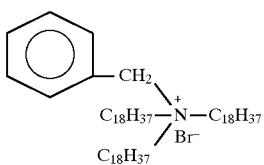

(XII)

Example X

The ionic gelator of Example III is utilized in the gelling of selected solvents. The procedure involves dissolving the gelator in the liquid to be gelled by heating. The mixture is then cooled to ambient temperature, which leads to gel formation. (The results are tabulated in Table I below).

TABLE I

Gelator Properties of
N-(3β-cholestanyl)-N-methyl-N,N-dioctadecylammonium iodide with Selected Solvents

| Liquid | wt % of gelator | phase formation | approximate stable period |
|---|---|---|---|
| Methanol | 0.8 | a | 6 hours |
|  | 1.0 | a | 1 day |
| 1-propanol | 1.0 | a | 12 days |
| 1/1(v/v)1-propanol/H$_2$O | 0.9 | a | >9 months |
| 1-octanol | 3.4 | b | 20 days |
|  | 1.0 | c |  |
| dodecane | 2.5 | b | >13 months |
|  | 1.0 | c |  |
| hexadecane | 2.5 | b | >13 months |
|  | 1.0 | c |  |
| tetrahydrofuran | 2.0 | b | >4 months |
| Dow-Corning silicone oil 704 | 2.0 | d | >13 months | a Transparent gels at room temperature.
b Translucent gels at room temperature.
c Solution upon heating, precipitation upon cooling to room temperature.
d A clear gel obtained after cosolvent CH$_2$Cl$_2$ is evaporated and the solution cooled to room temperature.

Example XI

The ionic gelator of Example VI is utilized in preparing various gels as set forth in Table II.

TABLE II

Gelator Properties of
N-methyl-N,N,N-trioctadecylammonium iodide

| Liquid | wt % of gelator | phase formation | stable time (RT) |
|---|---|---|---|
| styrene | 5.0 | transparent gel[a] | 30 minutes |
| toluene | 4.0 | solution[a] |  |
| benzene | 4.0 | solution[a] |  |
| 1-propanol | 4.3 | turbid gel[b] | 1 hours |
| 1-pentanol | 5.0 | turbid gel[b] | 4 hours |
| dodecane | 3.0 | turbid gel[b] | 3 months |
| hexadecane | 2.1 | turbid gel[b] | 3 months |
| dimethylsulfoxide | 3.0 | transparent gel[c] | 20 minutes |
| acetonitrile | 3.3 | precipitate[c] |  |
| Dow-Corning silicone oil 704 | 5.0 | transparent gel[d] | 5 months |

[a]Cooled by cold running water (18° C.).
[b]Gelled in an ice-bath.
[c]Cooled to room temperature in the air.
[d]Cooled to RT after the cosolvent CH$_2$Cl$_2$ is evaporated.

Example XII

The ionic gelator of Example VII is utilized in preparing various gels as set forth in Table III below.

TABLE III

Gelator Properties of
N-dodecyl-N,N,N-trioctadecylammonium iodide

| Liquid | wt % of gelator | phase formation | stable time (RT) |
|---|---|---|---|
| styrene | 2.8 | transparent gel[a] | 1 month |
| toluene | 4.0 | transparent gel[a] | 3 months |
| benzene | 3.0 | transparent gel[a] | 3 months |
| 1-pentanol | 3.3 | transparent gel[b] | 20 hours |
| 1-octanol | 3.0 | turbid gel[b] | 4 days |
| dodecane | 4.0 | translucent gel[b] | >6 months |
| Dow-Corning silicone oil 704 | 2.0 | transparent gel[c] | >5 months |

[a]Cooled to room temperature in air or under running water at 23° C.
[b]Cooled in ice water.
[c]Cooled to RT after the cosolvent $CH_2Cl_2$ is evaporated.

Example XIII

The ionic gelator of Example VIII is utilized in preparing various gels as set forth in Table IV below.

TABLE IV

Gelator Properties of
tetraoctadecylammonium iodide

| Liquid | wt % of gelator | phase formation | stable time (RT) |
|---|---|---|---|
| styrene | 4.0 | transparent gel[a] | 20 days |
| toluene | 4.0 | translucent gel[a] | 4 days |
| benzene | 3.0 | translucent gel[a] | 20 days |
| 1-propanol | 5.0 | precipitate[a] | |
| 1-pentanol | 3.4 | precipitate[a] | |
| dodecane | 4.0 | precipitate[a] | |
| acetonitrile | 2.5 | precipitate[a] | |
| Dow-Corning silicone oil 704 | 4.0 | precipitate[b] | |

[a]Cooled to room temperature in air or under running water at 23° C.
[b]Cooled to RT after the cosolvent $CH_2Cl_2$ is evaporated.

Example XIV

The ionic gelator of Example IX is utilized in the preparation of various gels as set forth in Table V below.

TABLE V

Gelator Properties of
N-benzyl-N,N,N-trioctadecylammonium bromide

| Liquid | wt % of gelator | phase formation | stable time (RT) |
|---|---|---|---|
| styrene | 5.0 | solution[a] | |
| 1-pentanol | 4.0 | solution[a] | |
| hexadecane | 4.0 | translucent gel[a] | 3 days |
| dodecane | 5.0 | translucent gel[a] | 3 days |
| dimethylsulfoxide | 4.0 | precipitate[b] | |
| Dow-Corning silicone oil 704 | 4.0 | transparent gel[b] | >13 months |

[a]Cooled to room temperature under running water at 25° C.
[b]Cooled to RT after the cosolvent $CH_2Cl_2$ is evaporated.

Examples XV and XVI

In these examples, gelator properties of N-ethyl-N,N,N-trioctadecylammonium iodide and N-butyl-N,N,N-trioctadecylammonium iodide in various liquids are summarized in Tables VI and VII.

TABLE VI

Gelator Properties of
N-ethyl-N,N,N-trioctadecylammonium iodide

| Liquid | wt % of gelator | phase formation | stable time (RT) |
|---|---|---|---|
| dodecane | 4.0 | turbid gel[a] | 2.5 months |
| styrene | 4.0 | transparent gel[a] | 2 months |
| benzene | 4.0 | translucent gel[a] | 6 months |
| Dow-Corning 704 silicone oil | 2.5 | transparent gel[b] | 2.5 months |
| 1-pentanol | 3.3 | precipitate[a] turbid gel[c] | 5 hours |
| cyclohexanol | 3.3 | turbid gel[a] | 2 hours |
| dimethyl sulfoxide | 2.5 | translucent gel[a] | 5 months |

[a]Cooled from isotropic solution to room temperature (RT) in the air.
[b]Cooled from isotropic solution to RT after a cosolvent $CH_2Cl_2$ was evaporated since the solid could not be dissolved when heated in the absence of $CH_2Cl_2$.
[c]Cooled from isotropic solution to 0° C.

TABLE VII

Gelator Properties of
N-butyl-N,N,N-trioctadecylammonium iodide

| Liquid | wt % of gelator | phase formation | stable time (RT) |
|---|---|---|---|
| dodecane | 4.0 | turbid gel[a] | 5 months |
| benzene | 4.0 | translucent gel[a] | 6 months |
| Dow-Corning 704 silicone oil | 3.3 | transparent gel[b] | 5 months |
| 1-pentanol | 3.3 | precipitate[a] turbid gel[c] | 3 days |
| cyclohexanol | 3.3 | translucent gel[a] | 5 months |
| dimethyl sulfoxide | 2.5 | precipitate[b] | |

[a]Cooled from isotropic solution to room temperature (RT) in the air.
[b]Cooled from isotropic solution to RT after a cosolvent $CH_2Cl_2$ was evaporated since the solid could not be dissolved when heated in the absence of $CH_2Cl_2$.
[c]Cooled from isotropic solution to 10° C.

Example XVII

The ionic gelator N,N,N,N-tetraoctadecylammonium bromide may be utilized in fabricating an organic zeolite and membrane material by the following process.

Styrene is polymerized and cross-linked while gelled by the ionic gelator N,N,N,N-tetraoctadecylammonium bromide. The polymerized gel may then be heated to a temperature below the glass transition temperature of the cross-linked polymer in a solvent that is capable of dissolving the gelator without appreciably swelling the polymer. Once the gelator is removed, a porous structure remains with numerous channels. The cross-sectional diameters in embodiments of the channels, because they have been formed by strands of the gelator, are of the same size as or greater than the strands that have been removed. The cross-sectional diameters in embodiments range from about 10 to about 100 nanometers, depending upon the gelator utilized, the number and length of alkyl chains on the gelator, the charge on the gelator, the nature of the counterion and the liquid polarity (gelator solubility) of the monomer liquid gelled.

The organic zeolites may be sectioned to provide membranes for the separation of macromolecular species and mesoscopic particles. Only those species/particles whose diameters are less than or equal to that of the (absent) gelator strand can pass through the membrane.

The organic zeolite can imbibe medicaments such as steroids, nicotine, and other medicaments by dissolving them in a solvent that does not swell appreciably the organic zeolite but allows the medicament to enter the pores of the zeolite (left by the absent gelator strands) via capillary action and diffusion. The solvent is then removed by evaporation, leaving the medicament within the pores. Controlled release of the medicament occurs through diffusion of the medicament to the surface of the zeolite which is placed in contact with the skin (as a patch) or is placed under the skin or in a muscle (as an implant).

Examples XVIII–XXI

To test gelation, an amine and liquid are heated in a sealed glass tube until the solid dissolves and then they are cooled. The macroscopic manifestation of successful gelation is the absence of observable flow when a sample is inverted. In many cases, gels were hazy or bluish due to the Tyndall effect. Gel stability is based upon the gelation temperature ($T_g$; measured by the "inverted flow" method) and the length of the period necessary to observe macroscopic phase separation when samples are incubated in sealed vials at room temperature.

At 2.5 wt %, the β-anomer of CDA forms a precipitate with dodecane and gels with Dow-Corning 704 silicone oil (tetramethyltetraphenyl-trisiloxane) or 1-pentanol, while the α-anomer produced only solutions. However, a translucent gel was obtained from 5 wt % α-CDA and silicone oil. The structurally simpler gelator, TOA, yields very stable gels with silicone oil or 1-pentanol, very unstable gels with benzene, and no gels with alkanes. Hydrogen-bonding to the lone-pair of electrons of the tertiary amines is not necessary for gelation.

Example XVIII

Methyldioctadecylamine ($CH_3N(C_{18}H_{37})_2$) forms stable gels with silicone oil and forms solutions in many other solvents such as dodecane, 1-pentanol, and benzene and is summarized in Table VIII.

TABLE VIII

Gelator Properties of methyldioctadecylamine

| Liquid | wt % of gelator | phase formation | stable time (RT) |
|---|---|---|---|
| dodecane | 4.0 | solution[a] | |
| benzene | 4.0 | solution[a] | |
| styrene | 5.0 | solution[a,b] | |
| Dow-Corning 704 silicone oil | 4.0 | translucent gel[b] | >1 month |
| 1-pentanol | 6.0 | solution[a] | |

[a]Cooled from isotropic solution to room temperature (RT) in the air.
[b]Cooled from isotropic solution to 10° C.

Example XIX

Trioctadecylamine (TOA) forms gels with silicone oils, 1-pentanol and 1-butanol, toluene, styrene, methyl macrylate, etc. and is summarized in Table IX.

TABLE IX

Gelator Properties of trioctadecylamine

| Liquid | wt % of gelator | phase formation | stable time (RT) |
|---|---|---|---|
| cylohexane | 3.7 | solution[a] | |
| hexadecane | 2.1 | precipitate[a,b] | |
| styrene | 5.0 | fracture gel[a] transparent gel[b] | >20 days |
| toluene | 4.0 | solution[a] translucent gel[c] | 10 min |
| benzene | 4.0 | solution[a] transparent gel[b] | 5 months |
| methyl methacrylate | 3.0 | transparent gel[a] | 3 months |
| Dow-Corning 704 silicone oil | 4.0 | transparent gel[d] | 5 months |
| | 2.5 | transparent gel[d] | >6 months |
| 1-pentanol | 5.0 | turbid gel[a] | |
| | 2.0 | turbid gel[a] | >1 month |
| dimethyl sulfoxide | 3.0 | precipitate[d] | |

[a]Cooled from isotropic solution to room temperature (RT) in the air.
[b]Cooled from isotropic solution to 10° C.
[c]Cooled from isotropic solution to 0° C.
[d]Cooled from isotropic solution to RT after a cosolvent, $CHCl_3$ was evaporated since the solid could not be dissolved when heated in the absence of $CHCl_3$.

Example XX

N-(3(β)-cholestanyl)-N-N-dioctadecylamine forms gels with silicone oil, benzyl alcohol, 1-pentanol to 1-decanol, toluene, styrene, methyl methacrylate, etc. and is simmarized in Table X.

TABLE X

Gelator Properties of N-(3(β)-cholestanyl)-N,N-dioctadecylamine

| Liquid | wt % of gelator | phase formation | stable time (RT) |
|---|---|---|---|
| dodecane | 4.2 | precipitate[a] | |
| styrene | 5.0 | transparent gel[b] | 10 hours |
| toluene | 4.0 | solution[a] turbid gel[b] | 6 minutes |
| methyl methacrylate | 3.0 | translucent gel[b] | 4 days |
| Dow-Corning 704 silicone oil | 3.8 | transparent gel[b] | |
| | 2.5 | transparent gel[b] | >2 months |
| 1-pentanol | 6.0 | turbid gel[a] | 5 months |
| 1-nonanol | 4.2 | turbid gel[a] | >5 months |
| 1-decanol | 4.2 | turbid gel[a] | >5 months |

[a]Cooled from isotropic solution to room temperature (RT) in the air.
[b]Cooled from isotropic solution to 0° C.

Example XXI

N-(3(α)-cholestanyl)-N,N-dioctadecylamine forms stable gels with silicone oil and forms solution in many other solvents such as dodecane, 1-pentanol, and benzene and is summarized in Table XI.

TABLE XI

Gelator Property of
N-(3(α)-cholestanyl)-N,N-dioctadecylamine

| Liquid | wt % of gelator | phase formation | stable time (RT) |
|---|---|---|---|
| hexane | 5.0 | phase formation[a] | |
| | | solution[a] | |
| hexadecane | 6.0 | solution[a] | |
| toluene | 4.0 | solution[a] | |
| methyl methacrylate | 3.0 | solution[a] | |
| Dow-Corning 704 silicone oil | 2.5 | translucent gel[b] | >2 months |
| 1-pentanol | 5.0 | solution[a] | |
| 1-nonanol | 5.0 | solution[a] | |

[a]Cooled from isotropic solution to room temperature (RT) in the air.
[b]Cooled from isotropic solution to 0° C.

The above results indicate that a variety of liquids may be gelled with the gelators of the present invention. Gels of benzene or toluene are stable for only about 30 min with trioctadecylammonium iodide, for hours with N-methyl-N,N,N-trioctodecylammonium iodide, for weeks with N,N,N,N-tetraoctadecylammoium iodide, and for months with N-dodecyl-N,N,N-trioctadecylammonium iodide. By contrast, N,N,N,N-tetraoctadecylammonium iodide does not gel dodecane, but N-methyl-N,N,N-trioctadecylammonium iodide, N-dodecyl-N,N,N-trioctadecylammonium iodide, and trioctadecylammonium iodide do very well. Both N-methyl-N,N,N-trioctadecylammonium iodide and N-dodecyl-N,N,N-trioctadecylammonium iodide make very stable gels with silicone oil, but N,N,N,N-tetraoctadecylammonium iodide and trioctadecylammonium iodide lead to precipitates. 1-Pentanol forms the most stable gels with trioctadecylammonium iodide followed (in order of decreasing stability) by N-dodecyl-N,N,N-trioctadecylammonium iodide, N,N,N,N-tetraoctadecylammonium iodide and N-methyl-N,N,N-trioctadecylammonium iodide. These results illustrate the marked influence that the gelator structure and the nature of the liquid have on the network of gelator strands and the stability of the gels.

Pairwise comparisons of N,N,N,N-tetraoctadecylammonium iodide and N,N,N,N-tetraoctadecylammonium bromide or trioctadecylammonium iodide and trioctadecylammonium chloride provide a probe of the influence of counterions on gelator properties. Unlike N,N,N,N-tetraoctadecylammonium iodide, N,N,N,N-tetraoctadecylammonium bromide (and N-benzyl-N,N,N-trioctadecylammonium bromide) gels dodecane and silicone oil. Its gels with toluene, benzene, and 1-pentanol are much more stable than those employing N,N,N,N-tetraoctadecylammonium iodide. However, whereas trioctadecylammonium iodide gels dodecane and 1-pentanol, trioctadecylammonium chloride produces only macroscopically phase-separated mixtures with these liquids.

Of the two "spherical" quaternary ammonium iodides, N,N,N,N-tetradodecylammonium iodide is the superior gelator with almost all of the liquids examined, including dodecane and silicone oil (which were not gelled by N,N,N,N-tetraoctadecylammonium iodide) and benzene and toluene (which are gelled less well by N,N,N,N-tetraoctadecylammonium iodide). However, at 3.4 wt % (the concentration of N,N,N,N-tetraoctadecylammonium iodide that led to a turbid gel), N,N,N,N-tetradodecylammonium iodide remained dissolved in 1-pentanol.

It follows from the nature of the gel phases that a necessary (but insufficient) requirement is that the neat gelator molecules be solids at the temperatures of their gels. Thus, the smallest tri(n-alkyl)amine capable of making gels of the type described herein at or above room temperature, must have longer chains than tridodecylamine, mp 15.7° C. However, there is no apparent correlation between $T_c$, the clearing temperatures of the neat ammonium salts (and tertiary amines), of the gelators set forth in FIG. 3 and the $T_g$ of their gels. Pertinent data for the ammonium salts that gel dodecane are included in FIG. 3. At 3–4 wt % of gelator, the $T_g$ values seem to be in a plateau region and amenable to comparisons. The salt, N-methyl-N,N,N-trioctadecylammonium iodide, has the highest $T_c$, but its $T_g$ values are lower than those of N,N,N,N-tetraoctadecylammonium bromide and N,N,N,N-tetradodecylammonium iodide. The tetraoctadecylammonium salt with the higher $T_c$, N,N,N,N-tetraoctadecylammonium iodide, has much lower $T_g$ values.

Figure 3:
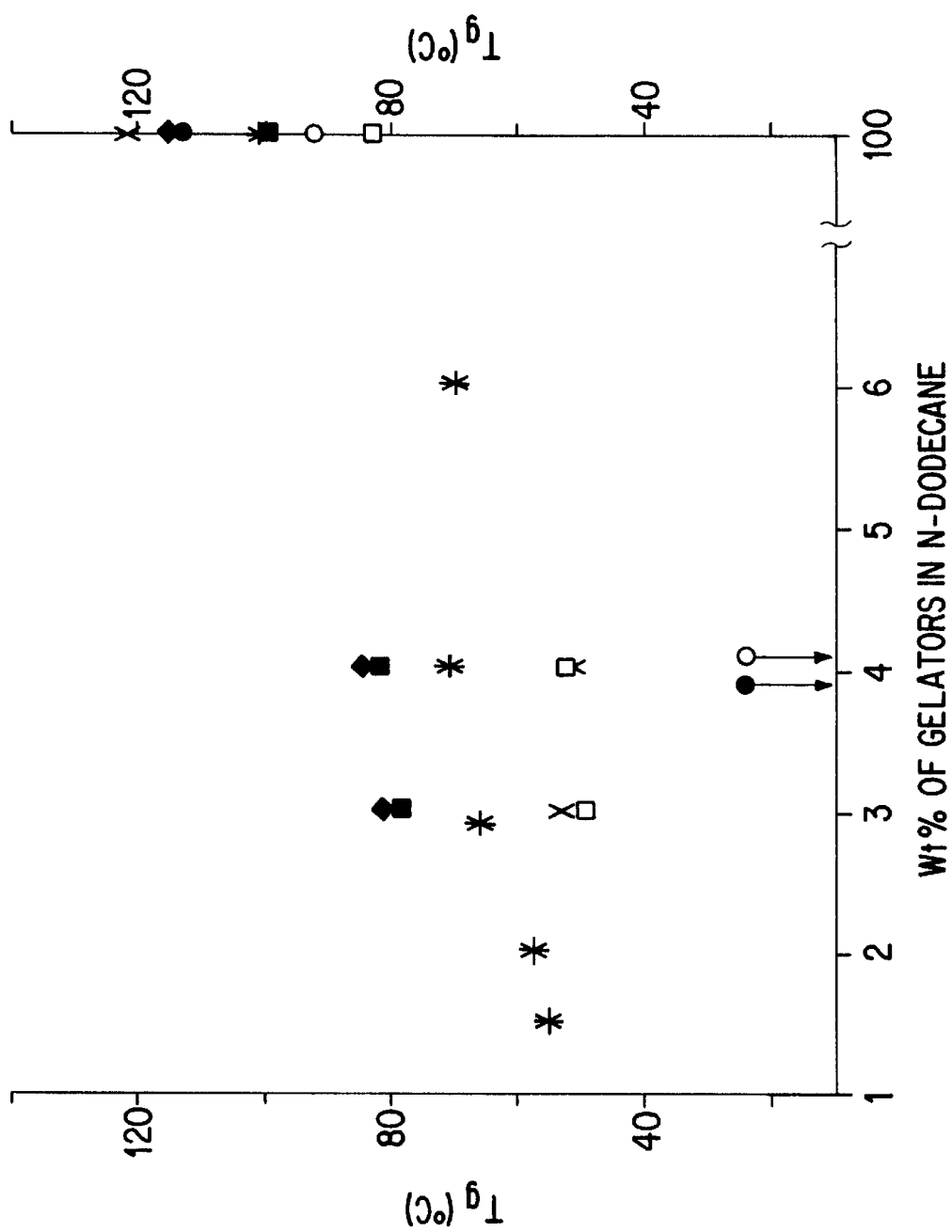
FIG. 3 represents a plot of neat gelator clearing temperatures ($T_c$) and median gelation temperatures ($T_g$) versus gelator concentration in n-dodecane of N-methyl-N,N,N-trioctadecylammonium iodide (designated as x), N-dodecyl-N,N,N-trioctadecylammonium iodide (designated as *), N,N,N,N-tetraoctadecylammonium iodide (designated as ●), N,N,N,N-tetraoctadecylammonium bromide (designated as ■), N-benzyl-N,N,N-trioctadecylammonium bromide (designated as ○), trioctadecylammonium iodide (designated as □) and N,N,N,N-tetradodecylammonium iodide (designated as ♦).

Many gelators are polymorphous, and the molecular packing in crystals from solvent recrystallization can be different from that in the strand networks of gels. Also, gelation temperature is very dependent upon gelator solubility in the liquid component; the relationship between the $T_g$ values of two gelators has been inverted by placing them in liquids of different polarity. Thus, no correlation between $T_c$ and $T_g$ should be expected in many cases. Some of the molecules of the gelators of FIG. 3 are mesomorphic. Again, there is no correlation between gelator efficiency and the ability of gelators to exist in more than one non-isotropic condensed phase.

What is claimed is:

1. A gelator for gelling polar and nonpolar liquids comprising at least one member selected from the group consisting of:

(A) compounds of the formula (I):

$$[R^1R^2R^3X-R^4]\pm Y\mp \qquad (I)$$

where $R^1$, $R^2$ and $R^3$ are the same or different and are hydrogen or organic groups selected from the group consisting of alkyl groups, alkenyl groups, alkynyl groups, aryl groups, arylalky groups, alkoxy groups, and aryloxy groups, wherein at least one of $R^1$, $R^2$ and $R^3$ represents an alkyl, alkenyl, or alkynyl group having at least 12 carbon atoms;

X is a Group IIIA or Group VA element;

$R^4$ is selected from the group consisting of a cholesteryl group, a cholestanyl group and derivatives thereof;

Y is a Group IA element or Group VIIA element selected from the group consisting of Cl, Br and I, or a Group IIA or VIA element.

2. A gelled polar or nonpolar liquid comprising said liquid and at least one gelator according to claim 1.

3. A gelator according to claim 1, wherein said organic groups are selected from the group consisting of $C_{12}$–$C_{30}$ alkyl radicals; $C_{12}$–$C_{30}$ alkenyl radicals; $C_{12}$–$C_{30}$ alkynyl radicals; $C_3$–$C_{30}$ cycloaliphatic radicals; aryl radicals; and arylalkyl radicals.

4. A gelator according to claim 1, wherein said organic groups are substituted with halogen selected from the group consisting of F, Br and I and oxygen substituents.

5. A gelator according to claim 1, wherein said organic groups are selected from the group consisting of alkyl, alkenyl and alkynyl radicals having from 12 to about 20 carbon atoms.

6. A gelator according to claim 1, wherein said organic groups are selected from the group consisting of alkyl, alkenyl and alkynyl radicals having from 12 to about 18 carbon atoms.

7. A gelator according to claim 2, wherein at least one of $R^1$, $R^2$ and $R^3$ comprises an alkyl, alkenyl or alkynyl radical having at least 15 carbon atoms.

8. A gelator according to claim 2, wherein when X represents a Group VA element, Y represents a Group VIIA element and when X represents a Group IIIA element, Y represents a Group IA element.

9. A gelator according to claim 2, wherein when X is a Group VA element, Y is a Group VIIA element.

10. A gelator according to claim 2, wherein when X is nitrogen, Y is iodide.

11. A gelator according to claim 2, wherein X is trivalent or tetravalent.

12. A gelator according to claim 2, wherein said compound is at least one member selected from the group consisting of:

(A) N- (3β-cholestanyl) -N,N-dimethyl-N-octadecylammonium iodide of the formula (IV):

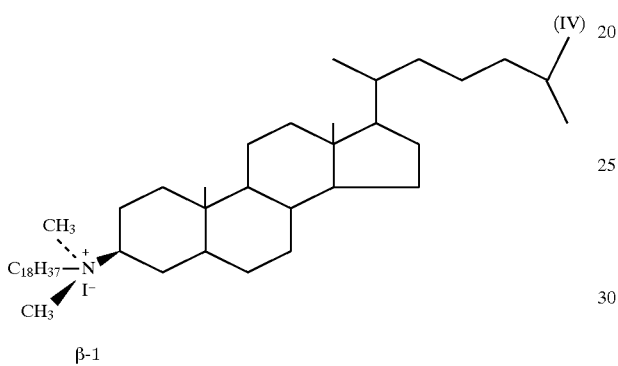

β-1

(B) N- (3α-cholestanyl) -N,N-dimethyl-N-octadecylammonium iodide of the formula (V):

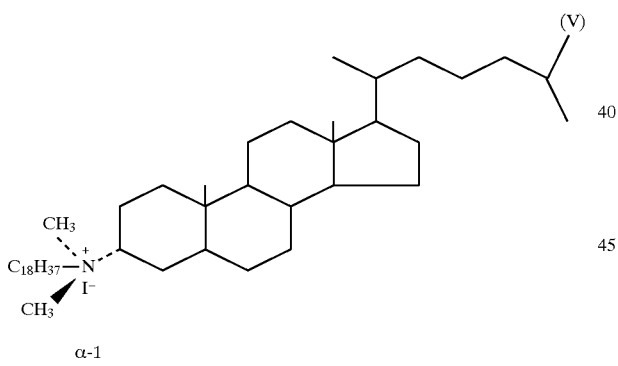

α-1

(C) N- (3β-cholestanyl) -N-methyl-N,N-dioctadecylammonium iodide of the formula (VI):

(D) N- (3α- cholestanyl) -N-methyl-N,N-dioctadecylammonium iodide of the formula (VII):

(E) N- (3β-cholestanyl) -N-methyl-N,N-dioctadecylammonium chloride of the formula (VIII):

13. A gelator according to claim 1, wherein said compound is N-(3β-cholestanyl)-N-methyl-N,N-dioctadecylammonium iodide of the formula (VI):

14. A gelled polar or nonpolar liquid, wherein said gelator is at least one member selected from the group consisting of:

(A) N- (3β-cholestanyl) -N,N-dimethyl-N-octadecylammonium iodide of the formula (IV):

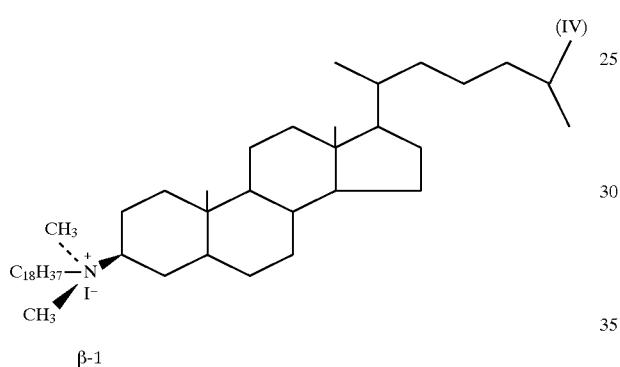

(B) N- (3α-cholestanyl) -N,N-dimethyl-N-octadecylammonium iodide of the formula (V):

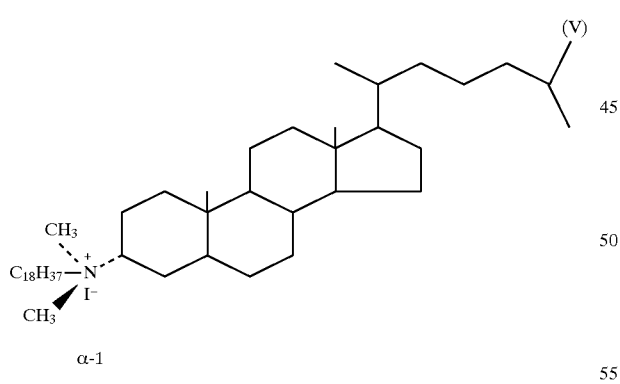

(C) N- (3β-cholestanyl) -N-methyl-N,N-dioctadecylammonium iodide of the formula (VI):

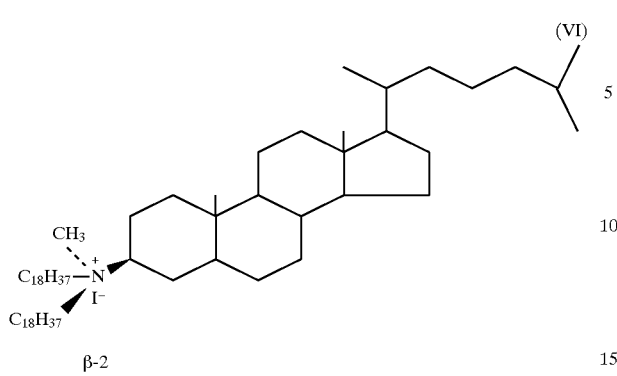

(D) N- (3α- cholestanyl) -N-methyl -N,N-dioctadecylammonium iodide of the formula (VII):

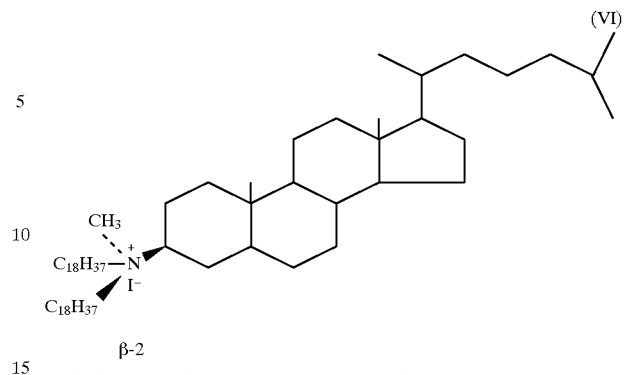

(E) N- (3β- cholestanyl) -N-methyl-N,N-dioctadecylammonium chloride of the formula (VIII):

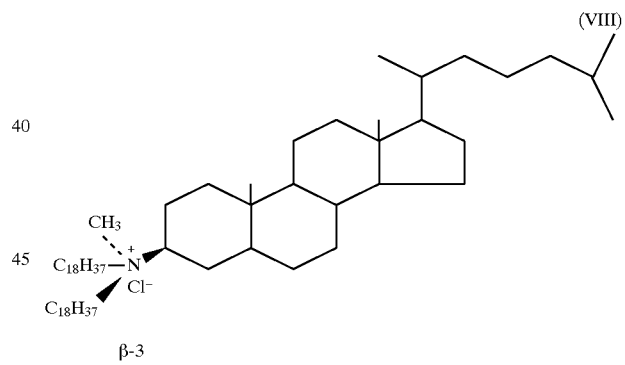

and derivatives thereof.

15. A gelled polar or nonpolar liquid according to claim 2, wherein said gelator is present in an amount of from about 0.05% to about 20% by weight based upon the liquid to be gelled.

16. A gelled polar or nonpolar liquid according to claim 2 wherein said gelator is present in an amount of from about 0.1% to about 2.0% by weight based upon the liquid to be gelled.

* * * * *